US005471993A

United States Patent [19]
Yoches et al.

[11] Patent Number: 5,471,993
[45] Date of Patent: Dec. 5, 1995

[54] METHOD OF MONITORING UTERINE ACTIVITY AND FETAL HEART RATE IN VETERINARY OBSTETRICS

[76] Inventors: Cheri C. Yoches, 3486 S. Chester Ct., Denver, Colo. 80231; Karen C. Snyder, 9111 W. 38th Ave., Wheat Ridge, Colo. 80033

[21] Appl. No.: 410,839

[22] Filed: Mar. 27, 1995

Related U.S. Application Data

[63] Continuation of Ser. No. 180,033, Jan. 11, 1994, Pat. No. 5,400,799.

[51] Int. Cl.⁶ ................................................. A61B 5/103
[52] U.S. Cl. .................................................. 128/778
[58] Field of Search ...................... 128/714, 715, 128/774, 775, 778, 782

[56] References Cited

U.S. PATENT DOCUMENTS

| | | | |
|---|---|---|---|
| 4,232,686 | 11/1980 | Kemmlede | 128/775 |
| 4,707,685 | 11/1987 | Carrier et al. | 128/775 |
| 5,042,503 | 8/1991 | Torok et al. | 128/778 |
| 5,070,888 | 12/1991 | Hon et al. | 128/778 |
| 5,205,296 | 4/1993 | Dukes et al. | 128/775 |
| 5,301,680 | 4/1994 | Rosenberg | 128/778 |

OTHER PUBLICATIONS

"Uterine Electromyographic Activity In Horse Mares As Measured by Radiotelemetry," Theriogenology, Mar. 1981 vol. 35, No. 3, pp. 591–601.

*Primary Examiner*—Max Hindenburg

[57] ABSTRACT

A method is disclosed for monitoring the uterine activity of an animal and the fetal heart rates. An electronic sensor is placed over the animal's abdomen and the detected signals are sent to a monitoring device which records the signals, for example, for display or transmission.

7 Claims, 4 Drawing Sheets

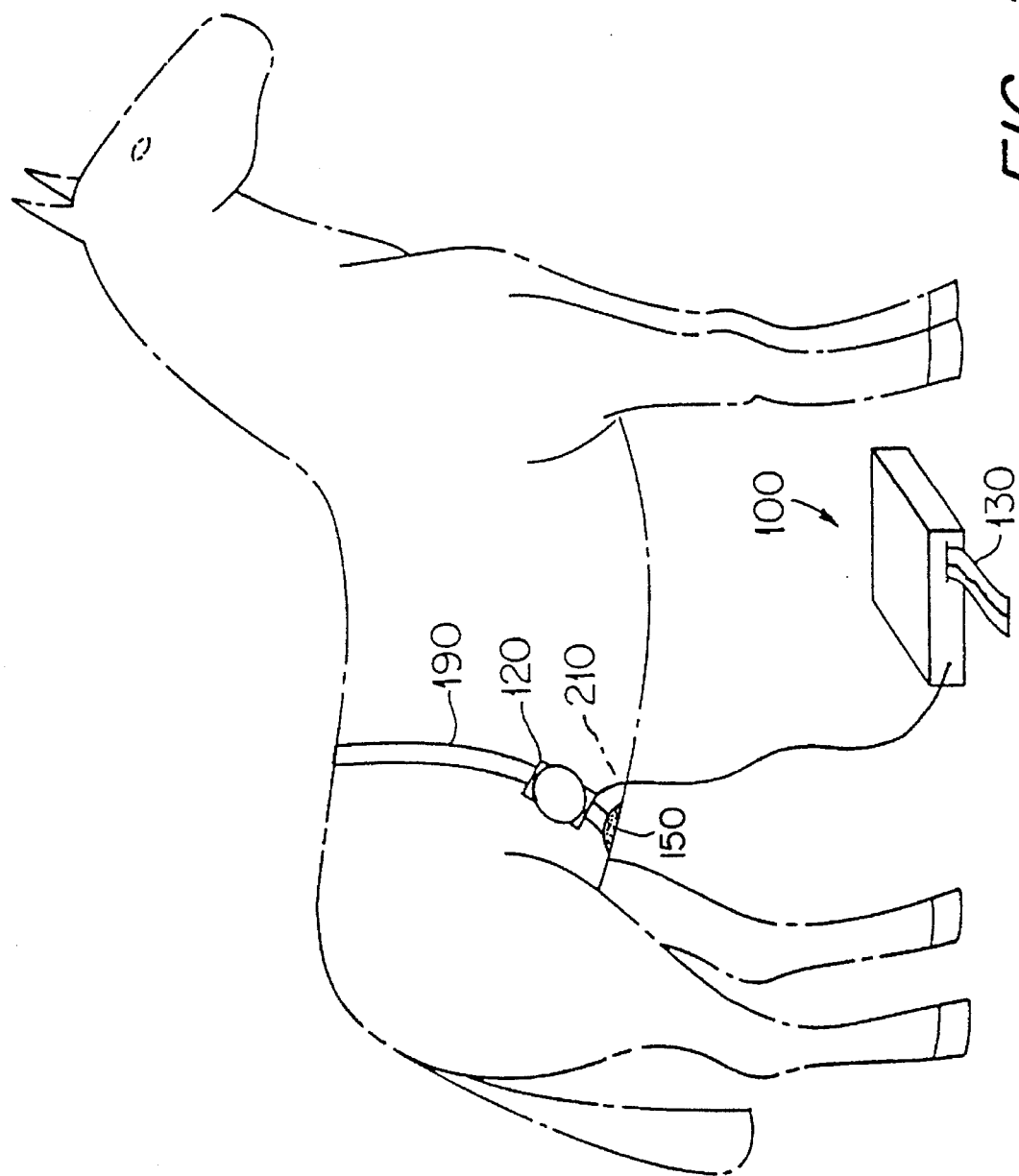

METHOD OF MONITORING UTERINE ACTIVITY AND FETAL HEART RATE IN VETERINARY OBSTETRICS

CONTINUATION DATA

This application is a continuation-in-part of U.S. Ser. No. 08/180,033, filed Jan. 11, 1994 to be issued as U.S. Pat. No 5,400,799.

BACKGROUND OF THE INVENTION

The present invention relates to the field of uterine monitoring for veterinary purposes and, more particularly, to such monitoring using electronic devices.

All mammals that deliver live offspring carry their fetus inside a uterus. As it grows and stretches to accommodate the fetus, the uterus periodically contracts. Studies of human pregnancies have shown that the frequency of these contractions will increase 24 to 48 hours prior to labor and delivery. Labor occurs when regular contractions dilate the cervix, the opening to the uterus, to allow delivery of the offspring through the birth canal.

The use of electronic devices to monitor human labor and delivery has been popular since the 1970's. Obstetricians often monitor the uterine activity of women to predict the onset of labor, both term and preterm, to ensure that proper precautions are initiated. Home monitoring of uterine activity has become increasingly popular, and is now advocated by many obstetricians and perinatologists.

Uterine monitoring uses a tocodynamometer to sense uterine irritability (a low amplitude, high frequency pattern) and uterine contractions. The tocodynamometer is placed outside a woman's body near the uterus. 3

In the 1980's, the design of the tocodynamometer improved sufficiently to allow patients at risk of preterm delivery to have their uterine activity monitored at home. The current home monitoring devices are much more sensitive to the detection of uterine activity than prior equipment used in a clinical setting to monitor term gestation. In fact, monitoring devices can now detect uterine activity as early as sixteen weeks into gestation.

For the most part, uterine monitoring has been limited to humans. One reason may be that delivery of human offspring takes so much longer delivery of other mammal offspring. For example, a typical human delivery averages twelve to fourteen hours from the onset of labor. A cow, on the other hand, calves in around three hours.

Veterinarians, animal owners, and other animal health care providers could benefit from monitoring uterine activity in animals to permit timely response, management, and treatment of animals during gestation, labor and delivery. The ability to herald the onset of labor before the animal exhibits the typical signs allows quicker response and preparedness on the part of the owner, caretaker, or veterinarian. Such uterine monitoring can be especially beneficial for animals in the growing speciality of planned animal reproduction because certain artificial inseminations are sufficiently valuable to warrant close evaluation of the subsequent pregnancy and general prenatal health of the animal.

There are many other conditions which threaten the viability of the mammal offspring that may benefit from uterine monitoring. These conditions include inducing or augmenting labor, multiple gestation, reproductive/infectious disease, a history of premature delivery of the offspring, uterine or pelvic abnormality.

SUMMARY OF THE INVENTION

Accordingly, it is desirable to monitor uterine activity in mammals to track gestation and delivery. This includes monitoring fetal heart rates. It is especially desirable to monitor fetal heart rate to assess fetal well being, both anteparten and intrapartum.

It is also desirable to detect and predict the onset of active labor as well as labor in its active stage.

Additional desires and advantages of the invention will be set forth in part in the description which follows, and in part will be obvious from the description, or may be learned by practice of the invention. The desires and advantages of the invention will be realized and attained by means of the elements and combinations particularly pointed out in the appended claims.

To achieve the objects and in accordance with the purpose of the invention, as embodied and broadly described herein, the invention comprises a method of monitoring uterine activity and fetal heart rate in a non-human mammal. The method comprises the steps of noninvasively positioning on the mammal a pressure-sensitive sensor for detecting uterine contractions in the mammal; positioning on the mammal a fetal heart rate sensor to detect the heart rate of a fetus inside the mammal; connecting the sensors to an electronic device for recording the uterine contractions of the mammal and the heart rate of the fetus; and periodically or continuously recording the uterine contractions of the mammal and the heart rate of the fetus using the electronic device. The position of the sensor is chosen on the mammal where the uterine contractions may be externally sensed, and fetal heart rate may be detected.

Both the foregoing general description and the following detailed description are exemplary and explanatory only and do not restrict the invention as claimed.

The accompanying drawings, which are incorporated in and constitute a part of this specification, illustrate one embodiment of the invention and, together with the description, serve to explain the principles of the invention.

BRIEF DESCRIPTION OF THE DRAWINGS

FIG. 2 shows the application of the device in FIGS. 1A and 1B to a horse.

DESCRIPTION OF THE PREFERRED IMPLEMENTATION

Reference will now be made in detail to the preferred implementation of the invention illustrated in the accompanying drawings. Wherever possible, the same reference numbers will be used throughout the drawings to refer to the same or similar parts.

The invention involves the use of a monitoring device to detect uterine activity and fetal heart rate in mammals, such as dogs, livestock, horses, exotics, and endangered animals, and to monitor fetal heart rates. The method is not only useful for assisting delivery, but also in gathering data to determine the onset of labor and delivery and predict premature labor and delivery. It may also be useful in managing the induction of the active labor phase. This method will be useful in establishing and monitoring fetal well being.

Figure 1A:
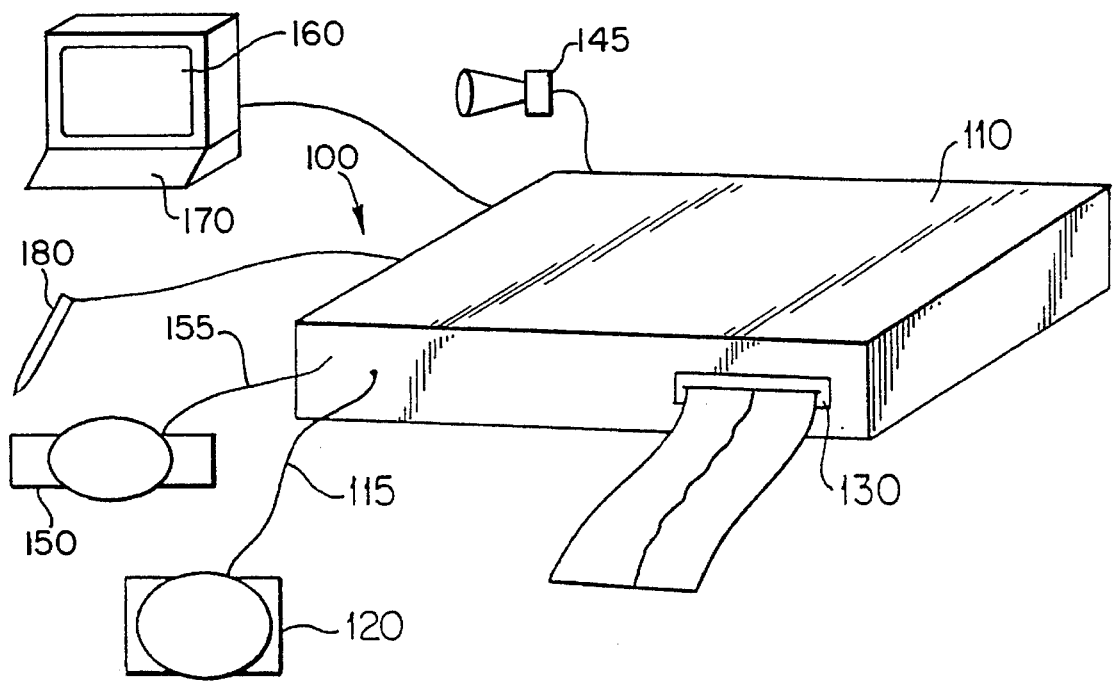
FIGS. 1A and 1B show the front and back views, respectively, of typical uterine contractions and fetal heart rate monitoring device that can be used with this invention.
Figure 1B:
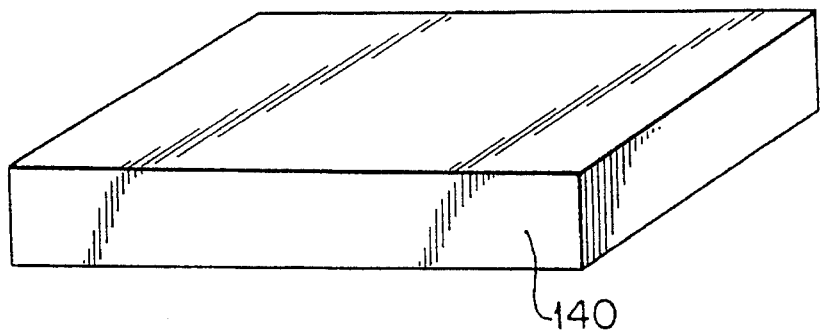

FIGS. 1A and 1B show the front and back views, respectively, of a monitoring device 100. Monitoring device 100 includes a monitor 110 connected to a sensor 120 via a cord 115. Sensor 120, which is known as a tocodynamometer, detects uterine contractions using a pressure-sensitive sensor that electromagnetically creates an electric signal. Cord 115 carries that electric signal to monitor 110. One example of sensor 120 is a Smyth-Guard Ring. Another is a microprocessor-driven sensor to perceive changes in interabdominal pressure. A third example might include a strain-gauge device.

Cord 115 is not required if sensor 120 is capable of transmitting a signal to monitor 110. A cordless sensor 120 could be worn continuously by the animal. The Smyth-Guard Ring or the interabdominal pressure sensor may be used in such an application.

In addition, the sensor could be programmed to gather and analyze data and alarm if the sensed signal deviated significantly from a baseline trace or when specific contraction patterns were noted. This alarm could also be transmitted through conventional means to a designated area, such as a clinic, a barn, or a house, or could signal a paging device or use cellular telephone technology.

Monitoring device 100 can also include a fetal heart rate sensor 150 to monitor the heart rate of fetuses and detect any signs of fetal distress. Sensor 150 may be part of a doppler system that uses ultrasound, and is preferably designed for particular species. Signals from sensor 150 may be carried by cord 155 or transmitted to monitor 110. Also, sensor 150 could analyze the detected heart rate signals and emit an alarm to warn of danger if the signals are out of normal parameter.

Monitor 110 processes the detected signals from sensors 120 and 150 for recording, display, transmission, or any other desired activity. Monitor 110 can include a strip chart recorder 130 or some other display device to show the detected signals in real time. Monitor 110 also may include a modem 140 to transmit the recorded signals to a remote facility over a standard telephone line, and to receive data from such a facility. Communication with a remote facility is especially useful for gathering data or seeking consultation.

Monitor 110 could also include a speaker 145 to provide an audible signal reflecting the heart rate tracing from sensor 150. Speaker 145 could also act as an alarm.

Monitor 110 could process the signals from several sensors 130 especially if they are cordless. In such an arrangement, the display connected to monitor 110 could show traces from several animals, or could store data for later analysis.

Another feature of monitor 110 is the display 160 and user input 170. Display 160 and user input 170, which can either be connected to monitor 110 or connected remotely, allow interactive assessment. Veterinarians or care provided can use input 170 to document physical changes such as behavior, nutrition, medication, temperature, udder development and colostrum development. A dipstick 180 can be used for colostral evaluation for calcium levels.

Monitoring device 100 should be light enough to carry into the field, yet durable enough to withstand use with animals. Although some modifications may be desirable to adapt human uterine monitoring devices to animal use, such modification should not change the basic operation of uterine activity and fetal heart rate monitoring.

FIG. 2 shows the use of monitoring device 100 with a pregnant horse. As FIG. 2 shows, sensor 120 of monitoring device 100 is placed on the abdomen 210 over the uterus and held in place with belt 190. To ensure the proper placement, the caregiver should be educated on proper sensor placement. In addition, strip chart recorder 130 can be used to indicate when a sufficiently strong signal has been detected.

Figure 3:
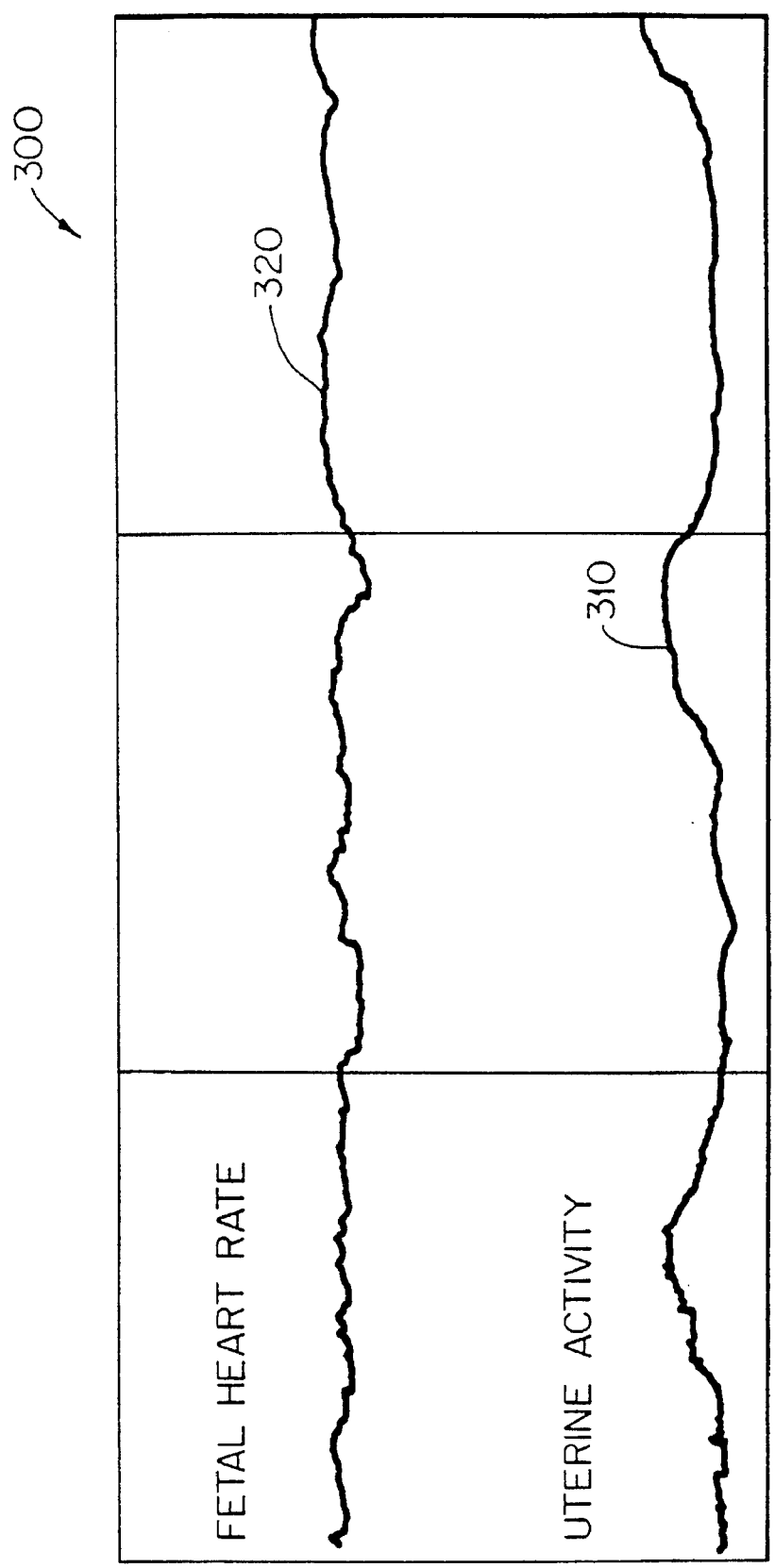
FIG. 3 shows typical strip recording of the uterine activity of an animal.

FIG. 3 shows an example of a strip chart 300 which may be obtained from monitoring the uterine activity of a horse and the fetal heart rate. Strip chart 300 includes a trace 310 for uterine activity as well as a trace 320 for fetal heart rate, which is an optional measurement.

Preferably, the caregiver should record data at least once daily for 30 minutes. More frequent or longer monitoring sessions may be performed based on the animal's individual needs.

Figure 4:
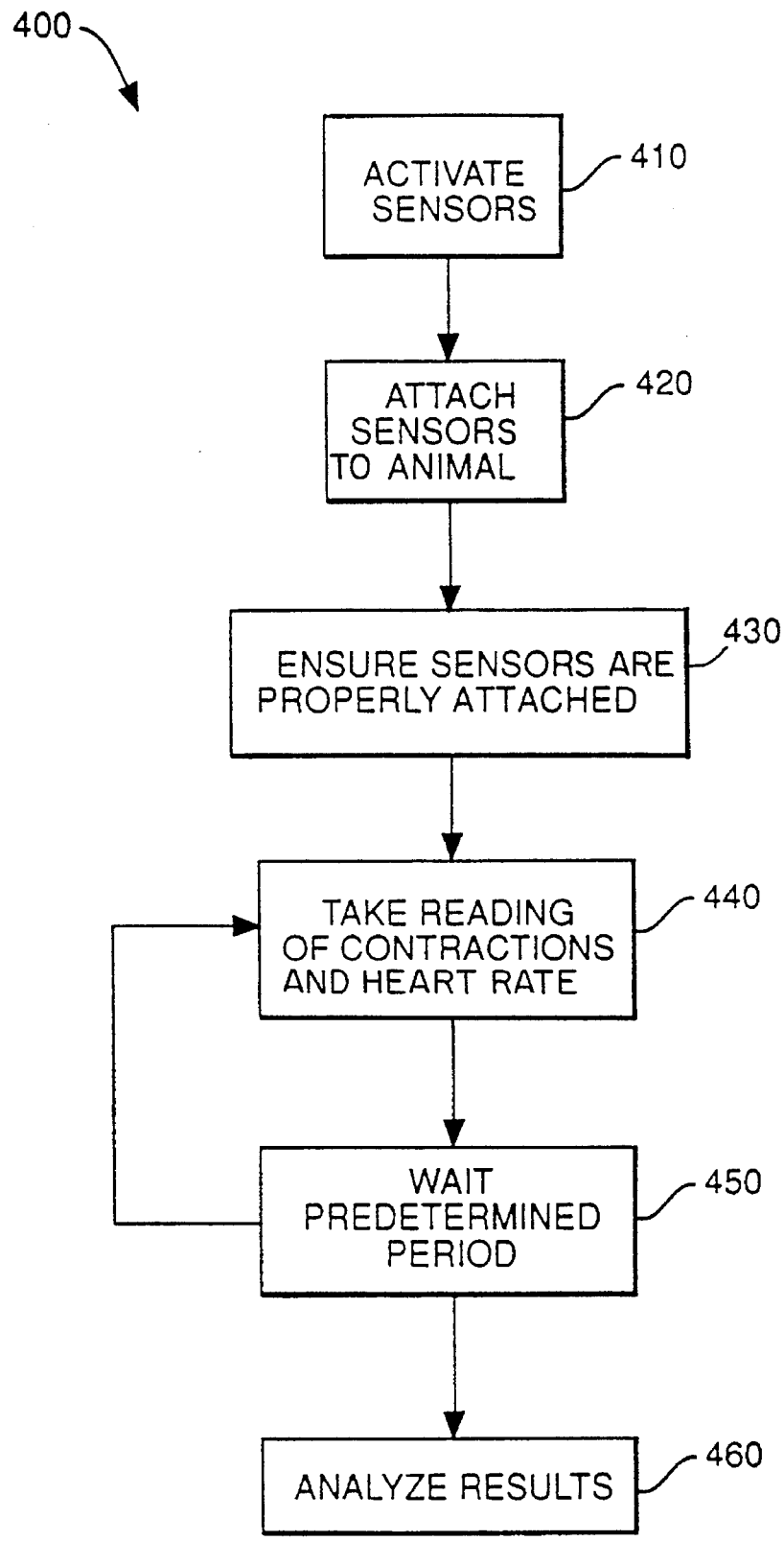
FIG. 4 is a flow diagram of the steps performed during monitoring.

FIG. 4 shows a detailed flow diagram 400 of the steps involved in monitoring the uterine activities of animals. First the sensors are activated (step 410), and then the belt with the sensors is attached to the animal and tightened around its abdomen (step 420). Checks are made to ensure that the sensors are properly attached (step 430), and then a reading is taken of the uterine contractions and the fetal heart rate (step 440). Such readings, as mentioned above, take ½ to 1 hours, or may run continuously. Readings are then taken periodically or continually based on the animal's needs, (step 450), and the data from such readings is analyzed at the appropriate facility step 460).

Use of this method will enable the practitioner access to data on an as needed basis without having to travel to the site unless the data or symptoms warrant a physical assessment. It may allow practitioners to care for several animals at one time, and will allow the owner or caretaker to be a more active participant in the care of their animal's pregnancy and management of labor and delivery.

This technology will also enable an owner or caretaker trained in the simple use of the equipment to record this data and send it to a practitioner for interpretation at another location. Such data will provide pertinent information to a veterinarian concerning the prenatal condition of the animal, and will be helpful in documenting uterine activity and fetal heart rate tracings.

What is claimed is:

1. A method of monitoring uterine activity and/or fetal heart rate in a non-human mammal comprising the steps of:

noninvasively positioning on the mammal a pressure-sensitive sensor for detecting uterine contractions in the mammal, the position of the sensor being chosen on the mammal where the uterine contractions may be externally sensed;

positioning on the mammal a fetal heart rate sensor to detect the heart rate of a fetus or fetuses inside the mammal;

connecting the sensors to an electronic device for recording the uterine contractions of the mammal and the heart rate of the fetus; and periodically recording the uterine contractions of the mammal and the heart rate of the fetus using the electronic device.

2. The method of claim 1 further including the step of transmitting the recorded uterine contractions and fetal heart rate of the mammal to a remote location.

3. The method of claim 1 wherein the step of recording the uterine contractions and fetal heart rate of the mammal includes the step of making a strip chart recording of the uterine contractions of the mammal.

4. The method of claim 1 wherein the step of connecting the sensors to the electronic device includes the step of using a cord.

5. The method of claim 1 wherein the step of connecting the sensors to the electronic device includes the step of establishing a cordless communications path.

6. The method of claim 1 further including the step of recording information via a user interface.

7. A method of monitoring uterine contractions and/or fetal heart rates for a plurality of non-human mammals comprising the steps of:

noninvasively positioning on each of the plurality of mammals a pressure-sensitive sensor for detecting uterine contractions of mammals, the positions of the sensors being chosen on the mammals where the uterine contractions may be externally sensed;

positioning on each of the mammals a fetal heart rate sensor to detect the heart rate of a fetus inside the mammal;

connecting the sensors to an electronic device for recording the uterine contractions of the mammals and fetal heart rates; and periodically recording the uterine contractions of the mammals and the fetal heart rates.

* * * * *